United States Patent
Rinehart et al.

[11] Patent Number: 6,124,293
[45] Date of Patent: Sep. 26, 2000

[54] SEMI-SYNTHETIC ECTEINASCIDINS

[75] Inventors: Kenneth L. Rinehart, Urbana, Ill.; Jose J. Morales, Bayamon, Puerto Rico

[73] Assignee: The Board of Trustees of the University of Illinois, Champaign, Ill.

[21] Appl. No.: 09/286,242

[22] Filed: Apr. 5, 1999

Related U.S. Application Data

[60] Provisional application No. 60/080,802, Apr. 6, 1998.

[51] Int. Cl.⁷ ........................ A61K 31/495; C07D 515/22
[52] U.S. Cl. ........................................... 514/250; 540/466
[58] Field of Search .................. 514/250; 540/466

[56] References Cited

U.S. PATENT DOCUMENTS

| | | | |
|---|---|---|---|
| 5,089,273 | 2/1992 | Rinehart et al. | 424/520 |
| 5,149,804 | 9/1992 | Rinehart et al. | 540/466 |
| 5,256,663 | 10/1993 | Rinehart et al. | 514/250 |
| 5,478,932 | 12/1995 | Rinehart et al. | 540/466 |
| 5,654,426 | 8/1997 | Rinehart et al. | 540/466 |
| 5,721,362 | 2/1998 | Corey et al. | 540/466 |
| 5,750,709 | 5/1998 | Castor | 546/348 |

*Primary Examiner*—Michael G. Ambrose
*Attorney, Agent, or Firm*—Ernest V. Linek; Banner & Witcoff, Ltd.

[57] ABSTRACT

The present invention is directed to several newly prepared semi-synthetic ecteinascidin (Et) species, designated herein as Et 757, Boc-Et 729, Iso-Et 743, Et 875, and Et 1560. The physical properties of these compounds, their preparation and bioactivities are also reported.

Et 757
$C_{40}H_{45}N_3O_{11}S$
Mol. Wt. 775

HRFAB:[M + H—H₂O]⁺ 758.2765 (Δ − 1.8 mDa)

Boc·Et 729

Iso-Et 743
$C_{35}H_{43}N_3O_{11}S$
Mol. Wt. 761.26

HRFAB:[M + H—H₂O]⁺ 744.2619 (Δ − 2.8 mDa)

Et 875
$C_{44}H_{49}N_3O_{14}S$
Mol. Wt. 875.94

HRFAB:[M + H]⁺ 875.2986 (Δ − 2.8 mDa)

-continued
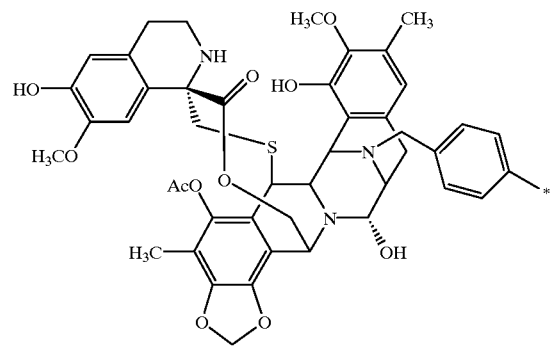
-continued
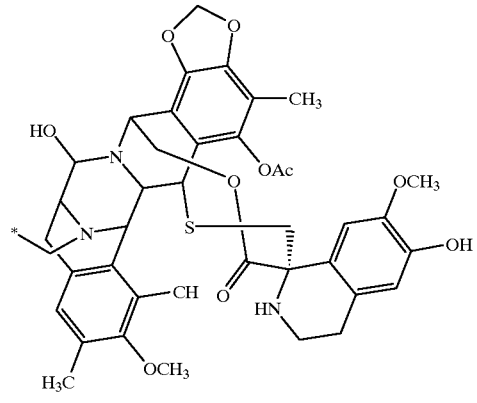
Et 1560
$C_{84}H_{38}N_6O_{22}S_2$
Mol. Wt. 1596
15 Claims, 12 Drawing Sheets

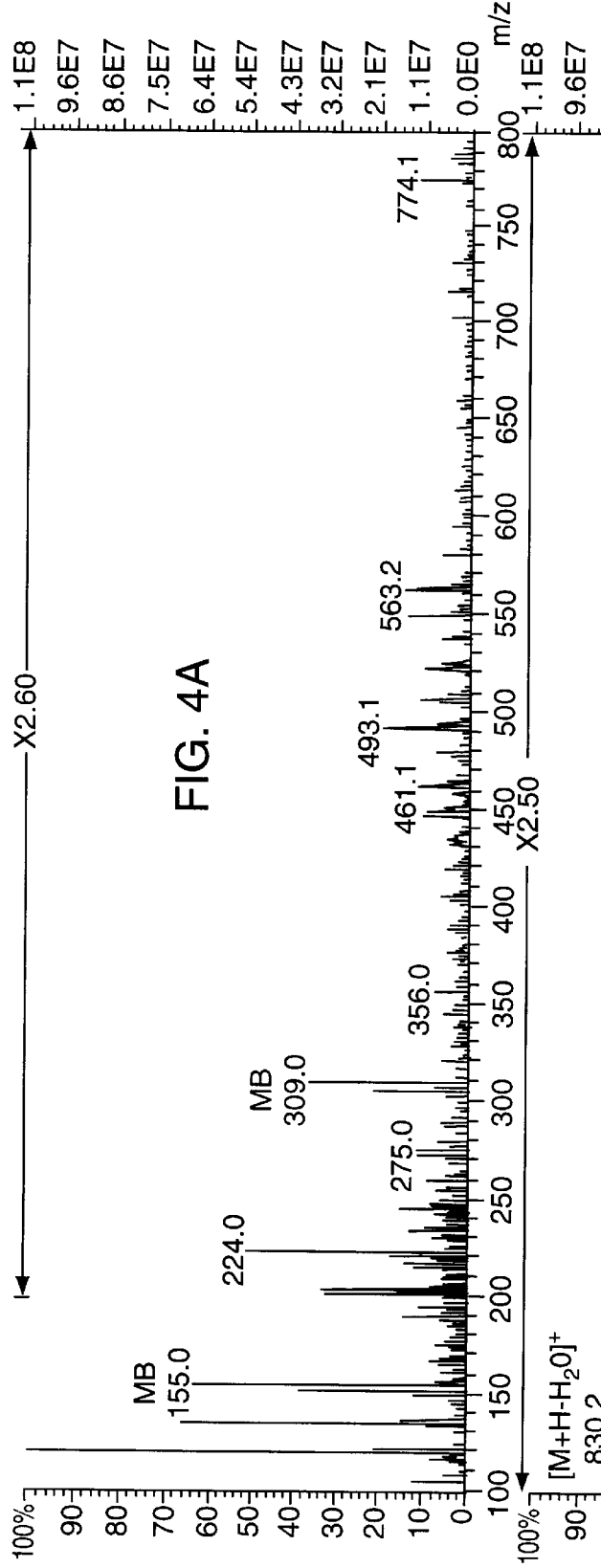
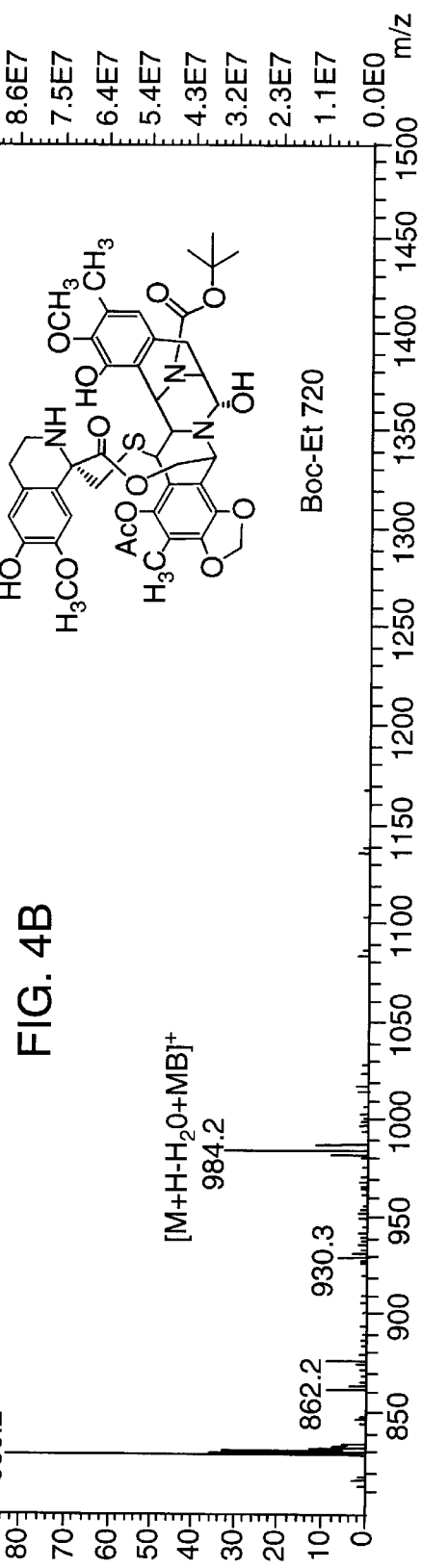
FIG. 4A
FIG. 4B
Boc-Et 720

SEMI-SYNTHETIC ECTEINASCIDINS

CROSS-REFERENCE TO RELATED APPLICATION

This application claims priority from provisional application, U.S. Ser. No. 60/080,802, filed Apr. 6, 1998, the disclosure of which is hereby incorporated herein by reference.

BACKGROUND OF THE INVENTION

The ecteinascidins (herein abbreviated Et or Et's) are exceedingly potent antitumor agents isolated from the marine tunicate *Ecteinascidia turbinata*. In particular, Et's 729, 743 and 722 have demonstrated promising efficacy in vivo, including activity against P388 murine leukemia, B16 melanoma, Lewis lung carcinoma, and several human tumor xenograft models in mice. The antitumor activities of Et 729 and Et 743 have been evaluated by the NCI and recent experiments have shown that Et 729 gave 8 of 10 survivors 60 days following infection with B16 melanoma. In view of these impressive results, the search for additional ecteinascidin compounds continues.

SUMMARY OF THE INVENTION

The present invention is directed to several new ecteinascidin compounds, prepared semi-synthetically, i.e., using previously discovered ecteinascidin compounds as the starting materials therefor. The structures of the new Et's of the present invention are as shown in Chart I below:

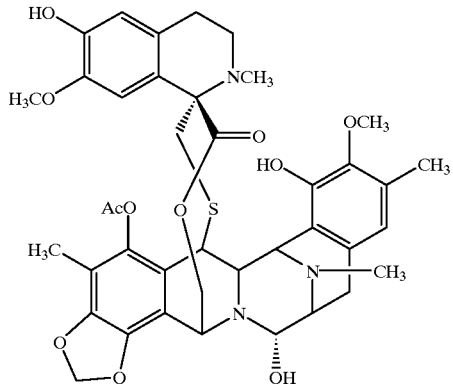

Et 757
$C_{40}H_{45}N_3O_{11}S$
Mol. Wt. 775

HRFAB:[M + H—H$_2$O]$^+$ 758.2765 (Δ – 1.8 mDa)

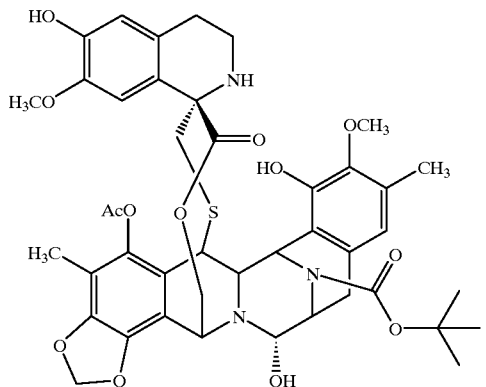

Boc•Et 729

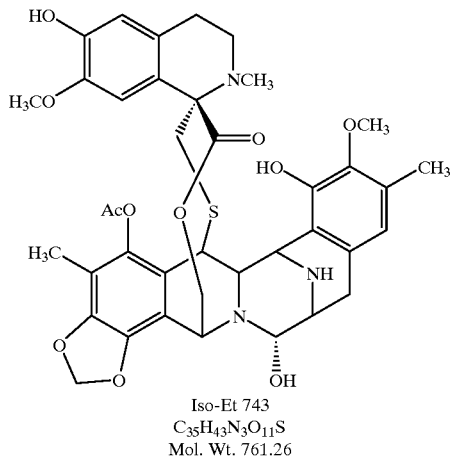

Iso-Et 743
$C_{35}H_{43}N_3O_{11}S$
Mol. Wt. 761.26

HRFAB:[M + H—H$_2$O]$^+$ 744.2619 (Δ – 2.8 mDa)

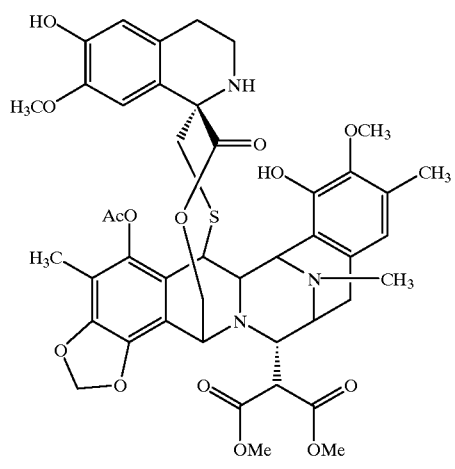

Et 875
$C_{44}H_{49}N_3O_{14}S$
Mol. Wt. 875.94

HRFAB:[M + H]$^+$ 875.2986 (Δ - 2.8 mDa)

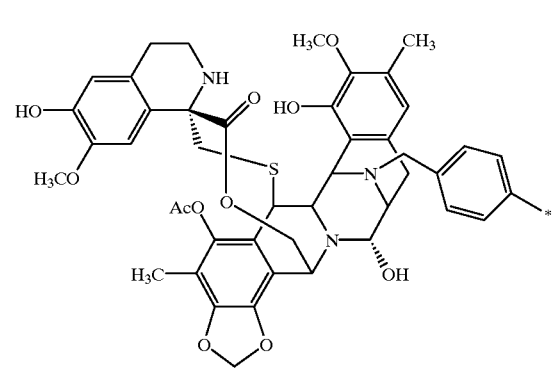

-continued

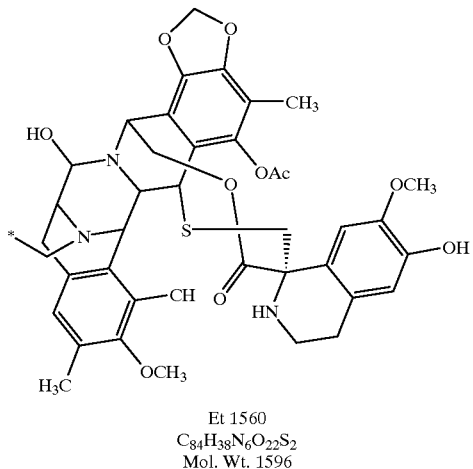

Et 1560
$C_{84}H_{38}N_6O_{22}S_2$
Mol. Wt. 1596

The new ecteinascidin compounds shown above have been found to possess similar antitumor activity profiles as the known ecteinascidin compounds, and as such they will be useful as therapeutic compounds, e.g., for the treatment of mammalian tumors including melanoma, lung carcinoma, and the like. The dosages and routes of administration will vary according to the needs of the patient and the specific activity of the active ingredient. The determination of these parameters is within the ordinary skill of the practicing physician.

BRIEF DESCRIPTION OF THE DRAWINGS

FIGS. 4A and 4B show the LRFAB Mass Spectrum of Et 729 in MB.

DETAILED DESCRIPTION OF THE PREFERRED EMBODIMENTS

As described above, a number of bioactive ecteinascidin compounds have been isolated from specimens of Ecteinascidia turbinata. See for example Ecteinascidins 729, 743, 745, 759A, 759B and 770, disclosed in U.S. Pat. Nos. 5,089,273 and 5,256,663, the disclosures of which are hereby incorporated herein by reference. See also, Ecteinascidins 736 and 722, disclosed in U.S. Pat. No. 5,149,804, which is hereby incorporated herein by reference. See also, U.S. Pat. Nos. 5,478,932 and 5,654,426, which are hereby incorporated herein by reference.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

EXAMPLE 1
Semi-synthesis of Et 757

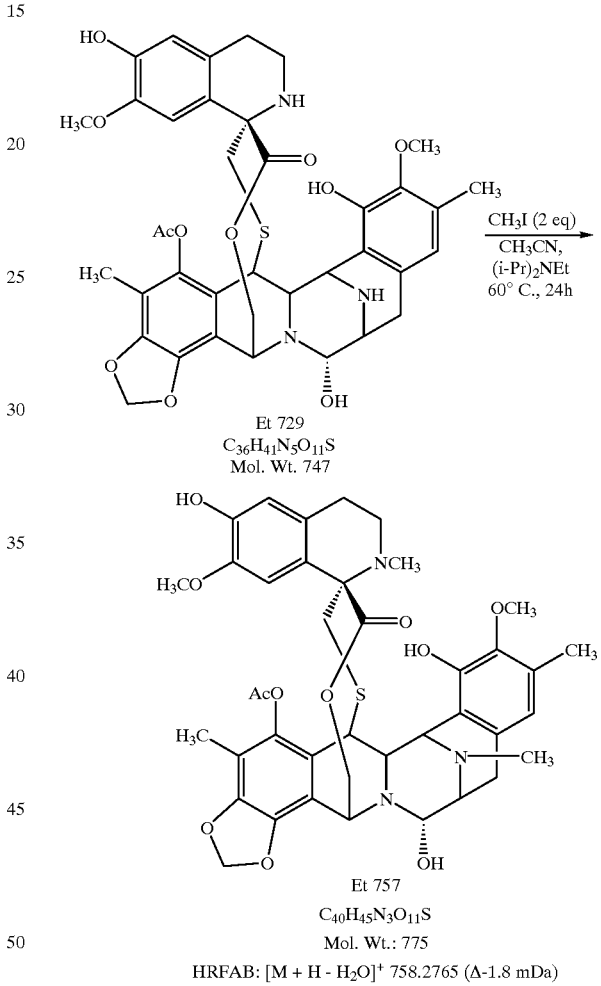

Et 729
$C_{36}H_{41}N_5O_{11}S$
Mol. Wt. 747

Et 757
$C_{40}H_{45}N_3O_{11}S$
Mol. Wt.: 775
HRFAB: $[M + H - H_2O]^+$ 758.2765 (Δ-1.8 mDa)

Figures 1A, 1B:
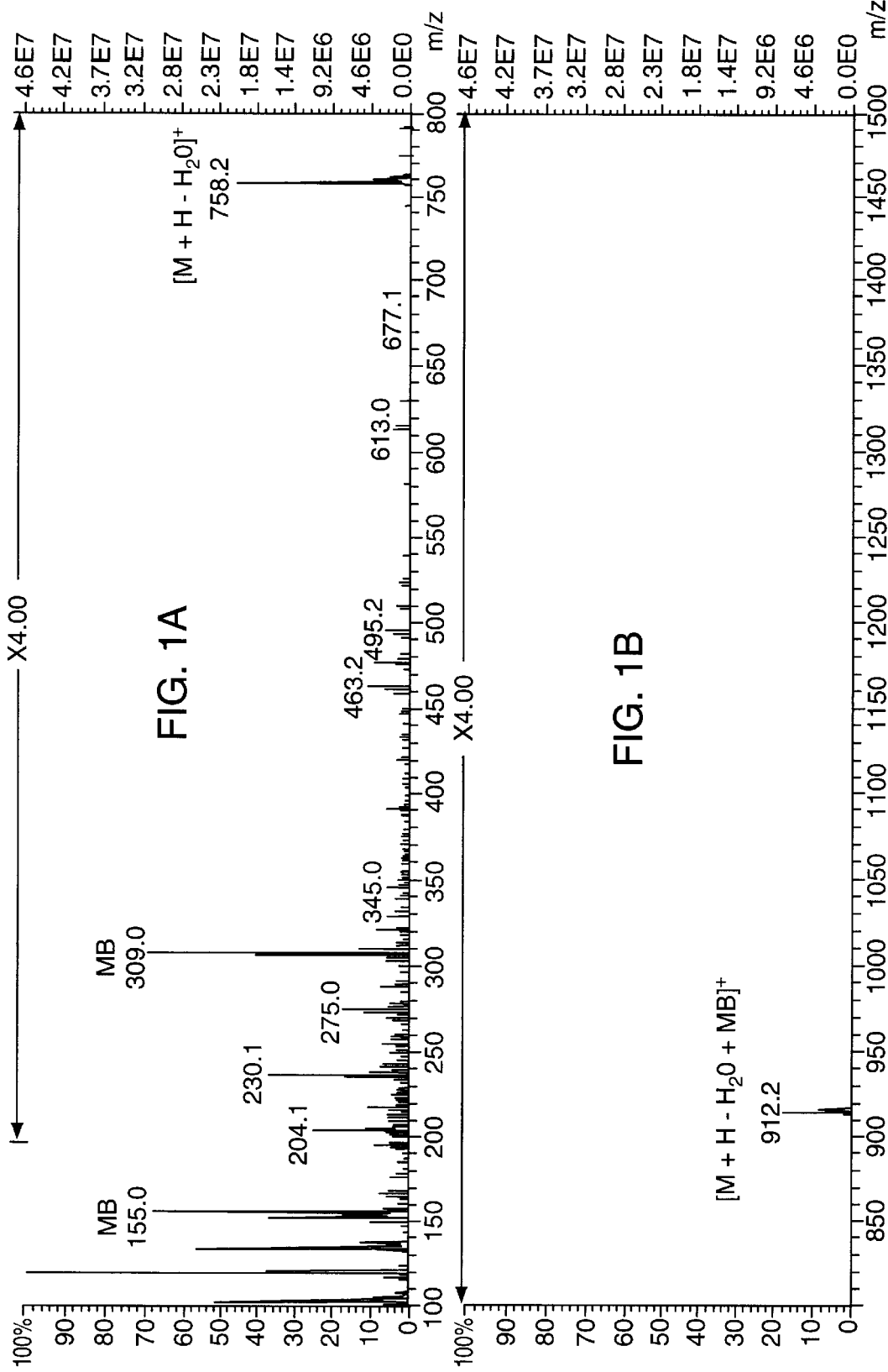
FIGS. 1A and 1B show the LRFAB Mass Spectrum of Et 757 in Magic Bullet (MB). See, Rinehart et al., Biochem, Biophys. Res. Commun., 1984, 124, 350.
Figure 2A:
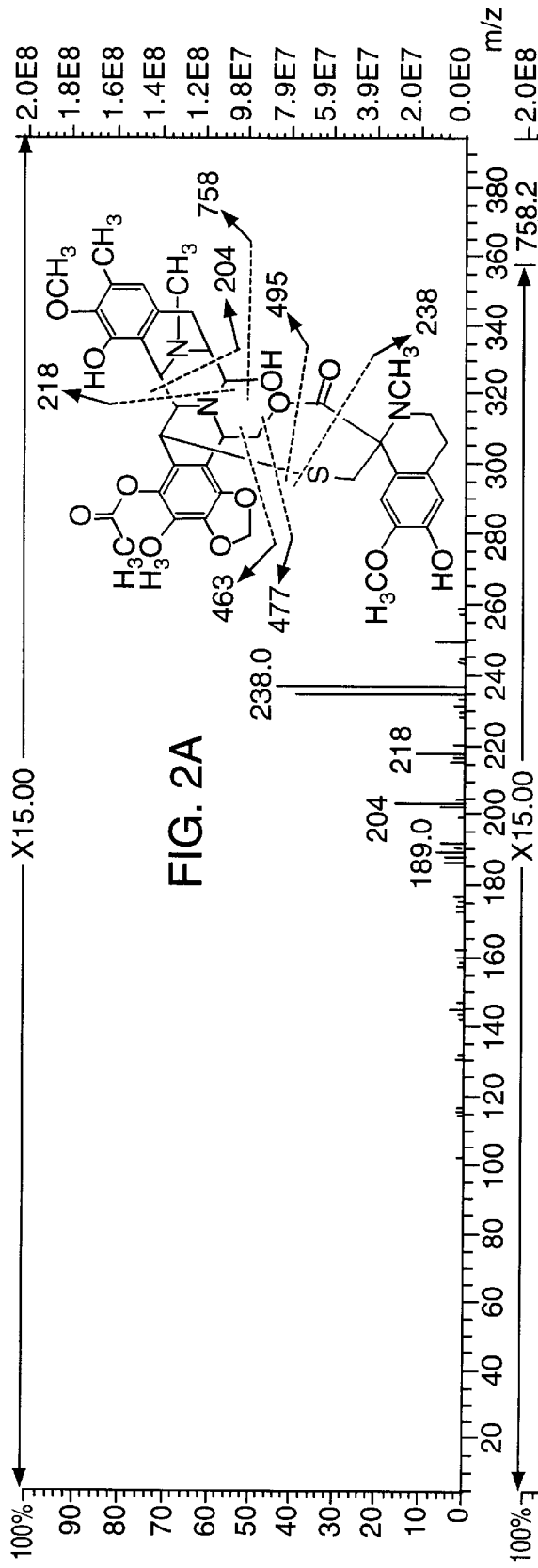
FIGS. 2A and 2B show the tandem FABMS/MS spectrum of Et 757 in MB.
Figure 2B:
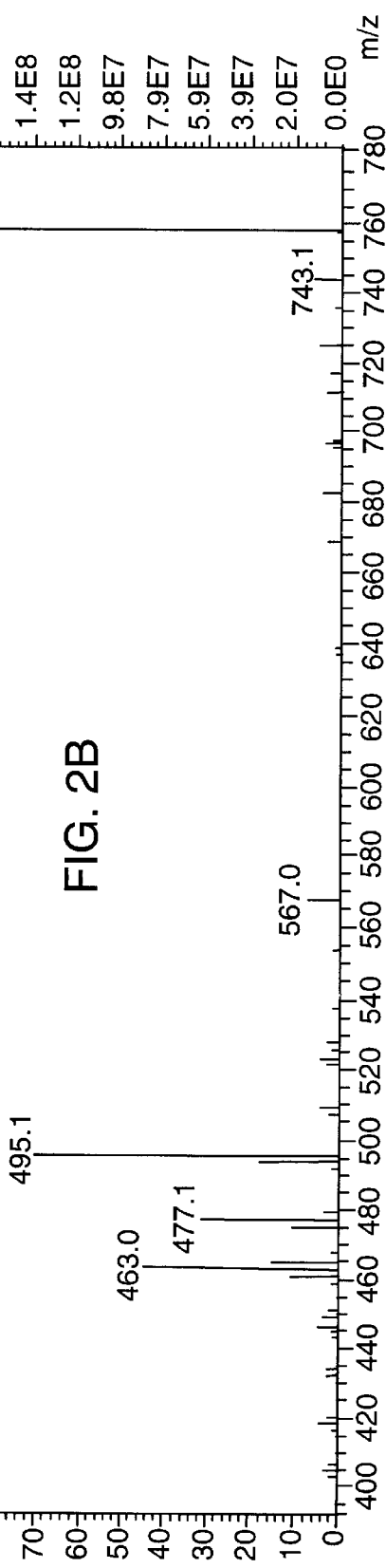
Figure 3:
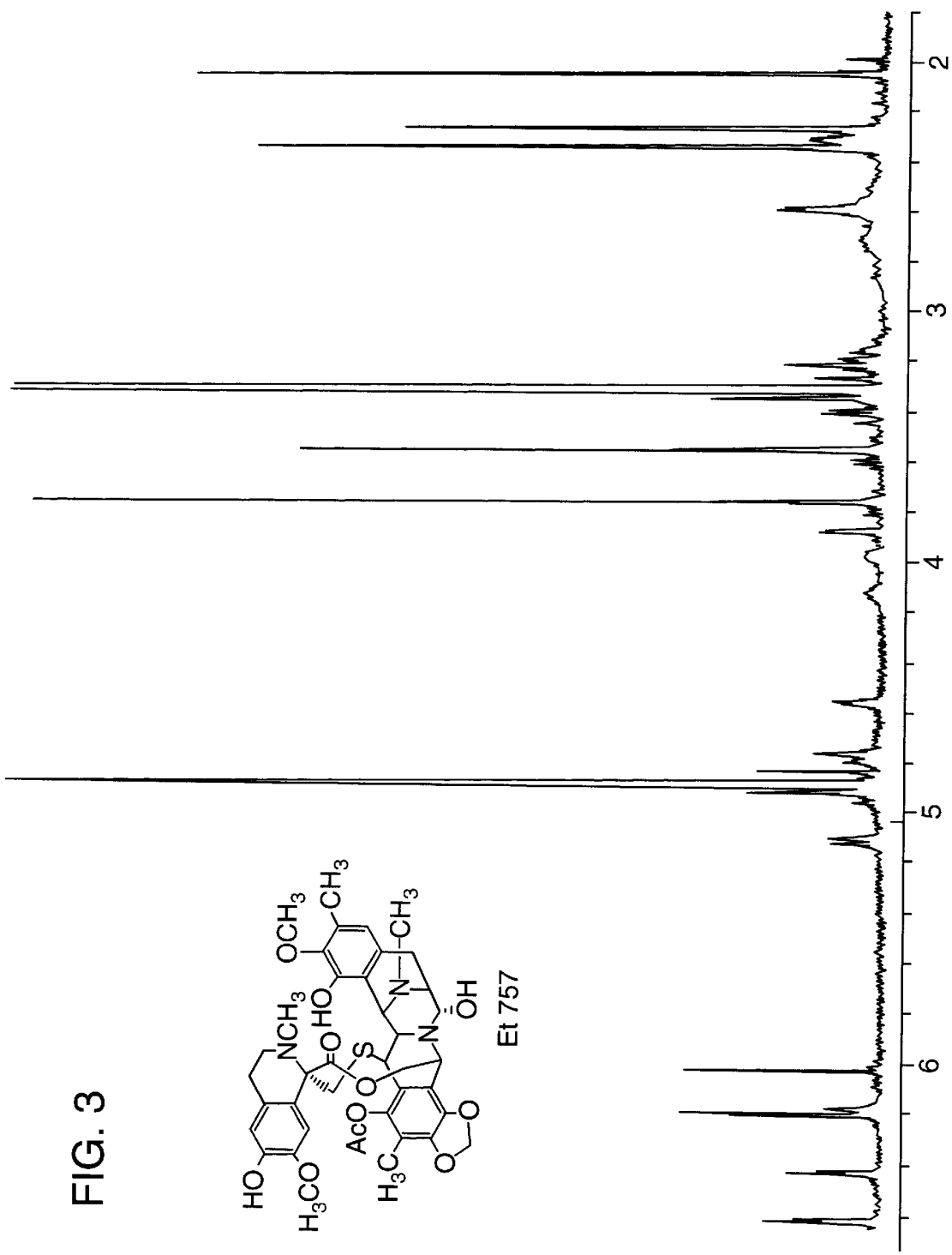
FIG. 3 shows the $^1$H NMR (500 MHz) spectrum of Et 757 in $CD_3OD$.

To a solution of Et 729 (9.2 mg, 0.012 mmol, 1 eq), diisopropylamine (12.9 μL, 0.074 mmol, 6 eq) and $CH_3CN$ (300 μL) was added $CH_3I$ (1.5 μL, 0.024 mmol, 2 eq) and the resulting solution was stirred at 60° C. for 24 hours. The reaction mixture was concentrated dryness under a nitrogen stream. The residue was purified by reversed phase HPLC (Phenomenex/Ultracarb-ODS, 2 mL/min) using 75% MeOH/$H_2O$ containing 0.02 M NaCl as mobile phase to yield Et 757 (2.2 mg, 24%) and Et 743 (2.3 mg, 25%) and a complex mixture of permethylated products. Et 757 was further purified by HPLC (Ultracarb-ODS) using 60% MeOH/$H_2O$ with 0.02 M NaCl as mobile phase to afford pure Et 757 (1.4 mg, 15%). HRFABMS, Calcd for $C_{40}H_{44}N_3O_{10}S$ $[M+H-H_2O]^+$ m/z 758.2747, Found 758.2765, see FIGS. 1 and 2; $^1$H NMR, see FIG. 3.

EXAMPLE 2
Semi-synthesis of Iso-Et 743

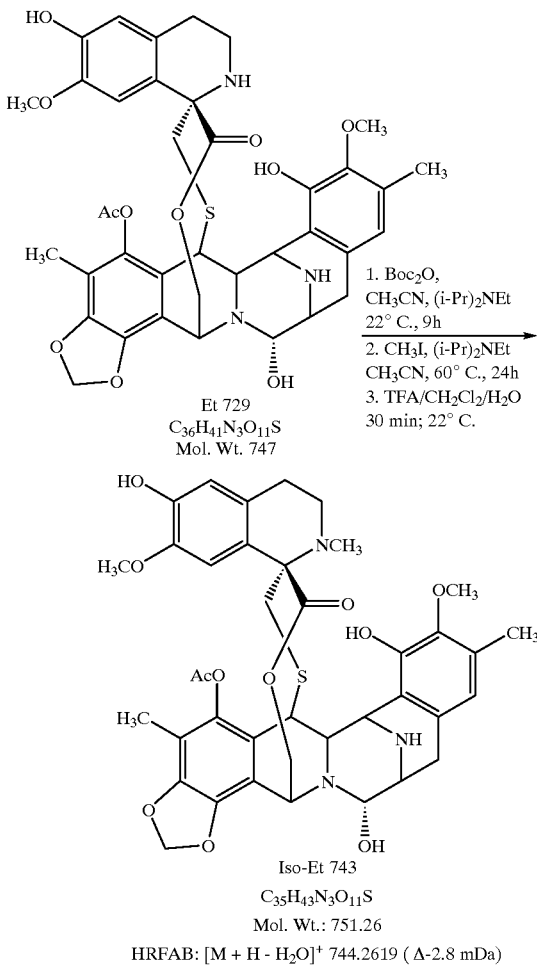

Step A—Boc-Et 729

Figures 5A, 5B:
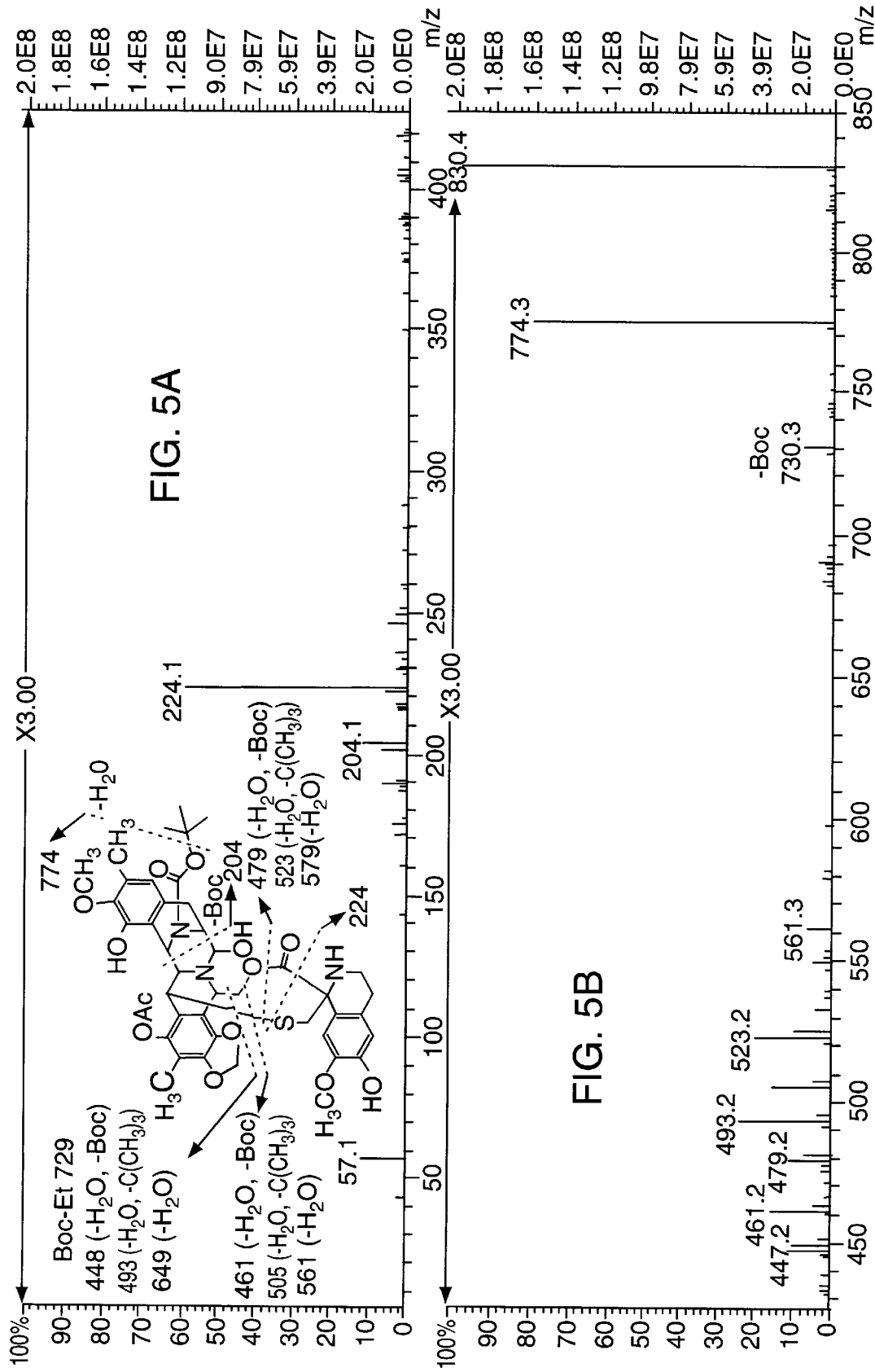
FIGS. 5A and 5B show the tandem FABMS/MS spectrum of Boc-Et 729 in MB.

To a solution of Et 729 (12.5 mg, 0.017 mmol, 1 eq), diisopropylethylamine (1.5 μL, 0.07 mmol, 4 eq) and $CH_3CN$ (300 μL) was added di-tert-butyl dicarbonate (3.6 mg, 0.017 mmol, 1.0 eq) and the resulting solution was stirrred at room temperature for 9 hours. The reaction mixture was concentrated to dryness under a nitrogen stream. The residue was purified by flash chromatography (gradient elution: 100% $CHCl_3$→90% $CHCl_3$/MeOH) to aford Boc-Et 729 (11.6 mg, 91%, $R_f$ 0.53 in 90% $CHCl_3$/MeOH); HRFABMS, Calcd for $C_{43}H_{48}N_3O_{12}S$ $[M+H]^+$ m/z 830.2958, Found 830.2942, see FIGS. 4 and 5.

Step B—Iso-Et 743

Figure 6:
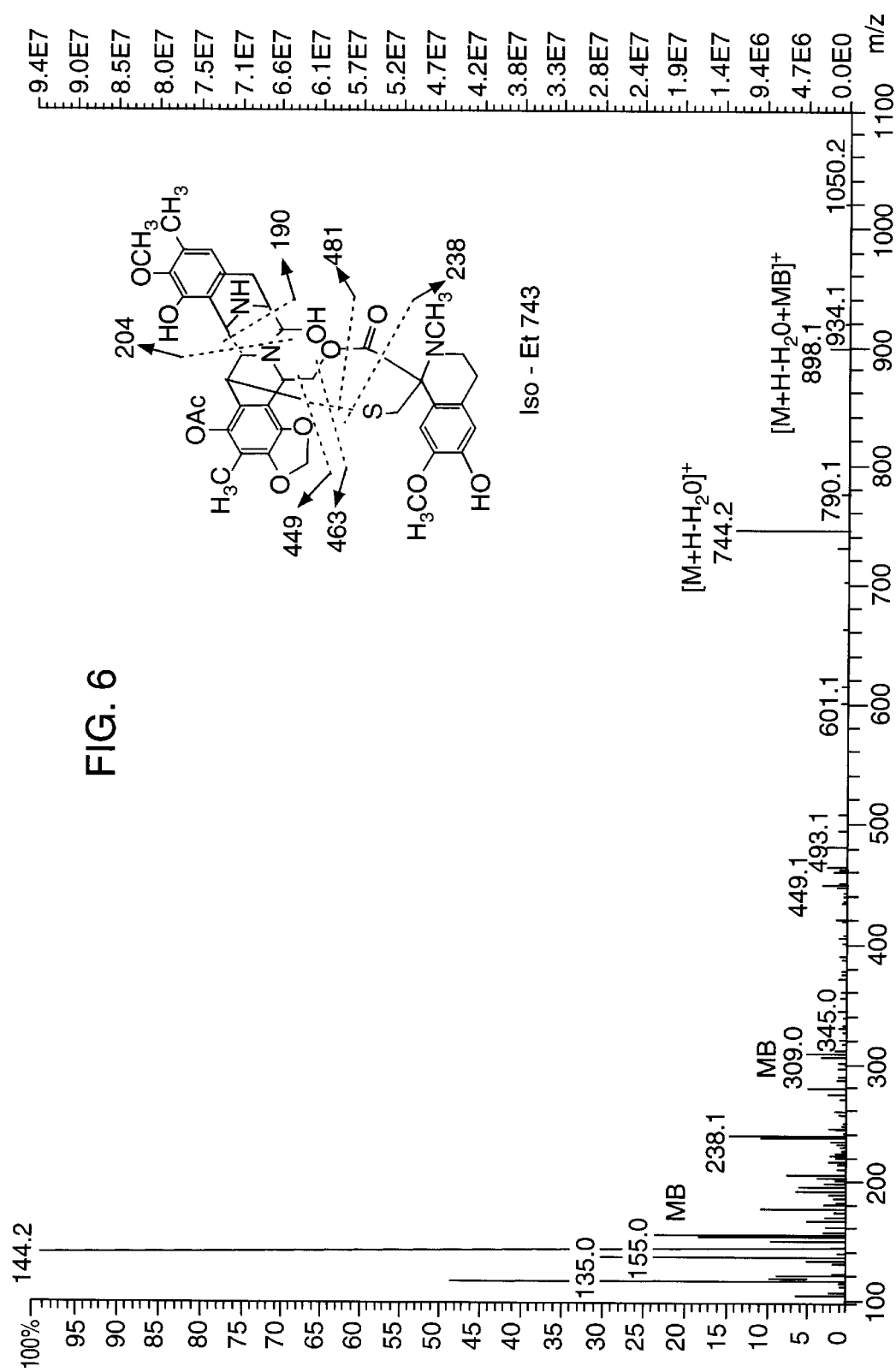
FIG. 6 shows the LRFAB Mass Spectrum of Iso-Et 743 in MB.
Figures 7A, 7B:
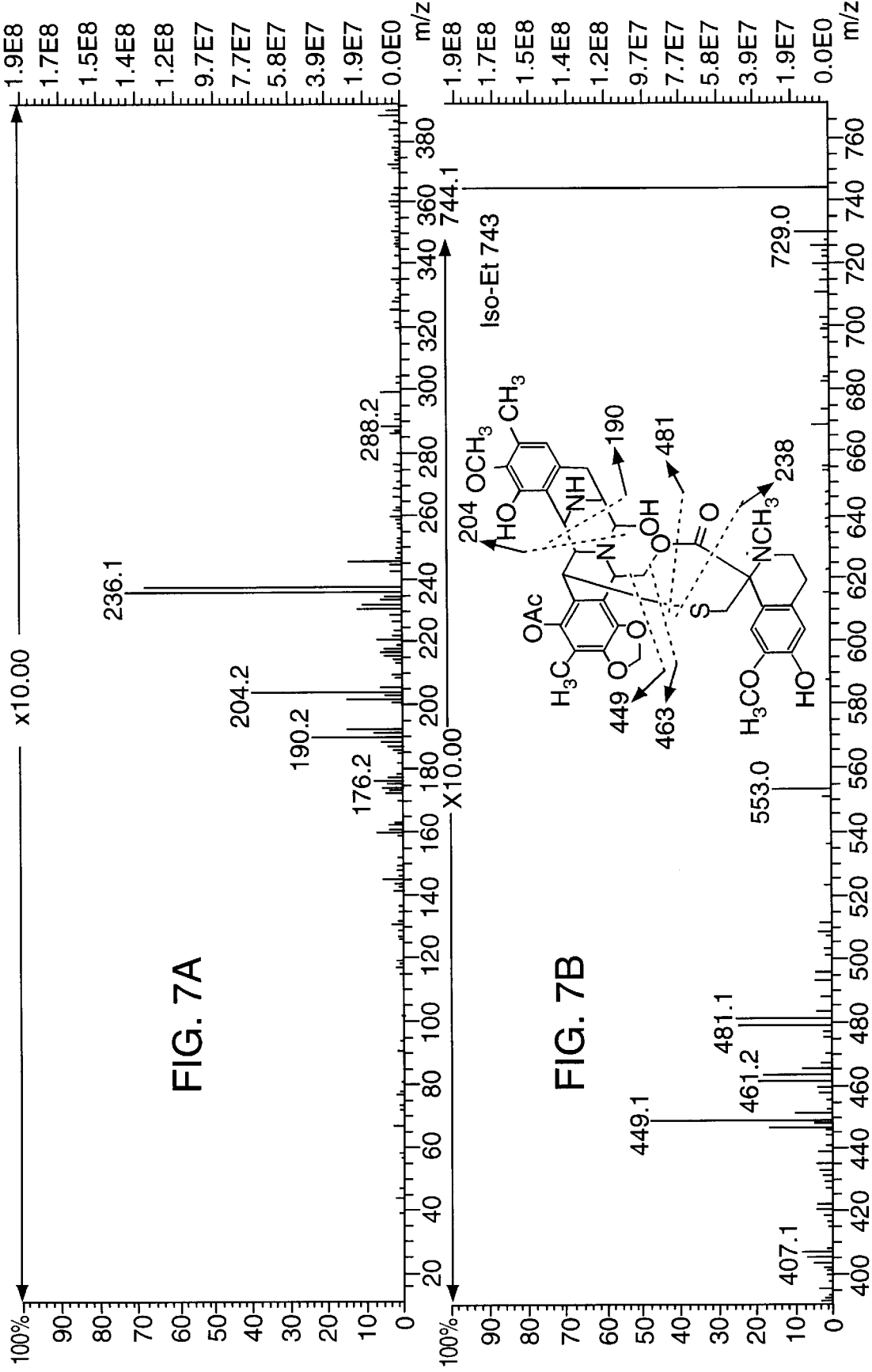
FIGS. 7A and 7B show the tandem FABMS/MS spectrum of Iso-Et 743 in MB.
Figure 8:
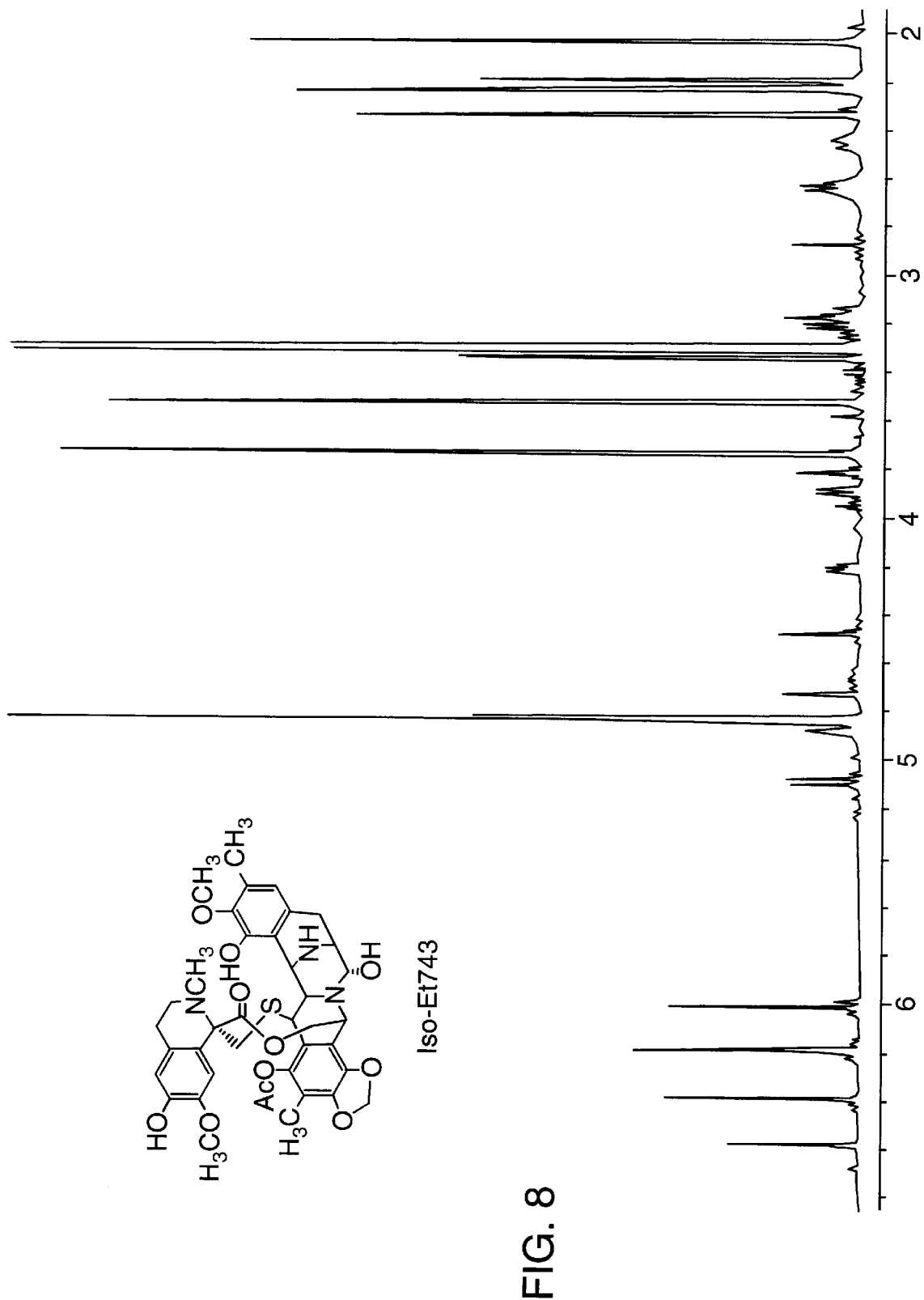
FIG. 8 shows the $^1$H NMR (500 MHz) spectrum of Iso-Et 743 in $CD_3OD$.
Figure 9:
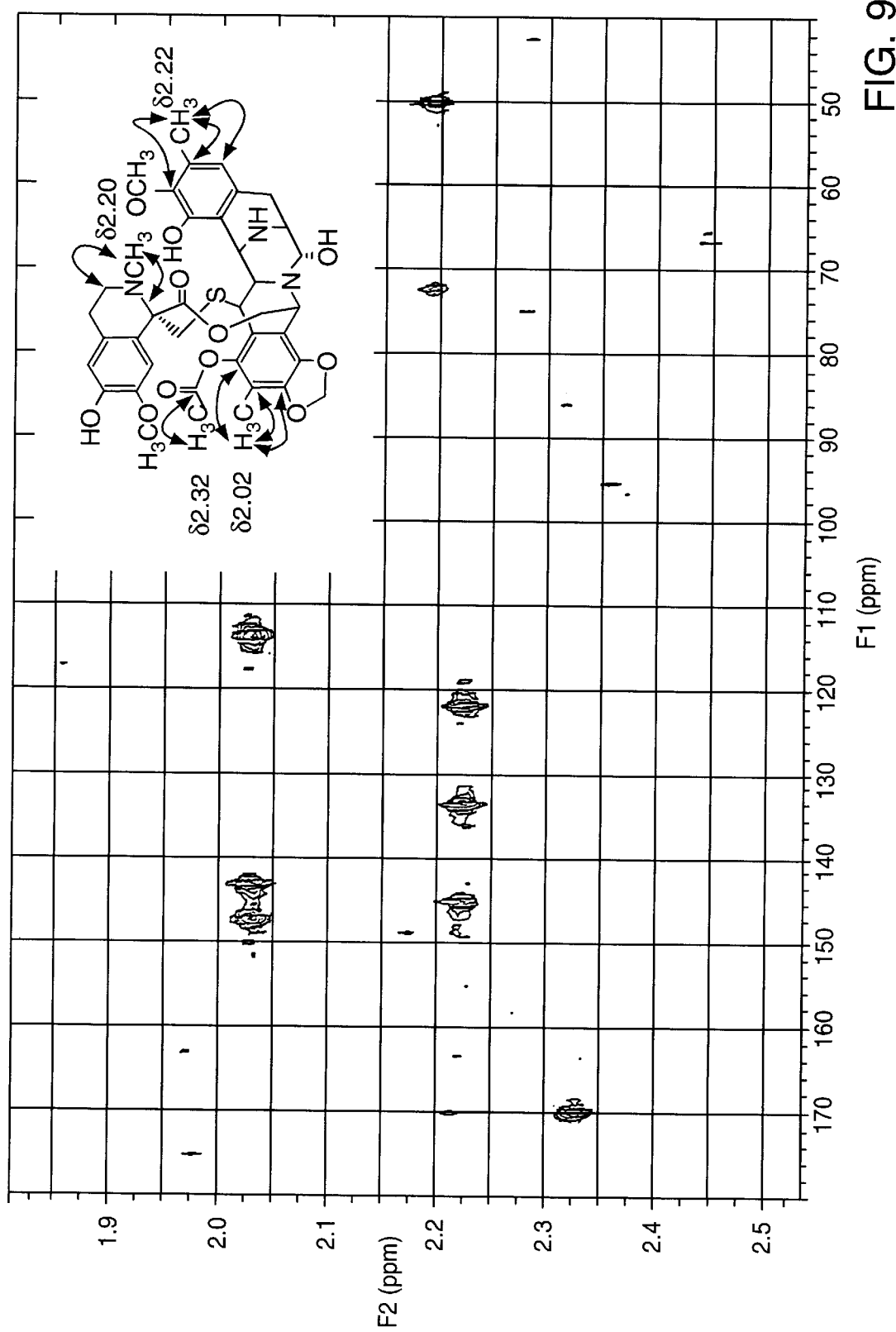
FIG. 9 shows expansion of the HMBC (750 MHz) spectrum of Iso-Et 743 in $CD_3OD$.

To a reaction flask containing Boc-Et 729 (11.6 mg, 0.014 mmol, 1 eq), diisopropylethyl amine (7.1 μL, 0.041 mmol, 3 eq), 500 μL of $CH_3CN$ and a magnetic stirrer was added $CH_3I$ (2.1 mg, 0.015 mmol, 1.1 eq), and the resulting solution was stirred at 60° C. for 24 hours. The reaction mixture was concentrated to dryness under a nitrogen stream, then 700 μL of $TFA/CH_2Cl_2/H_2O$ (4:1:1) was added. After the mixture was stirred at room temperature for 30 minutes, it was concentrated to dryness under a nitrogen stream. The residue was purified by reversed phase HPLC (Alltech-C18, 2 mL/min) using 60% $MeOH/H_2O$ containing 0.02 M NaCl as mobile phase to yield Iso-Et 743 (1.9 mg, 28%, based upon recovered Et 729) and unreacted Et 729 (3.6 mg). HRFABMS, Calcd for $C_{39}H_{42}N_3O_{10}S$ [M+H−$H_2O]^+$ m/z 744.2591, Found 744.2619, see FIGS. 6 and 7; $^1$H NMR and HMBC, see FIGS. 8 and 9 respectively.

EXAMPLE 3

Semi-synthesis of Et 875

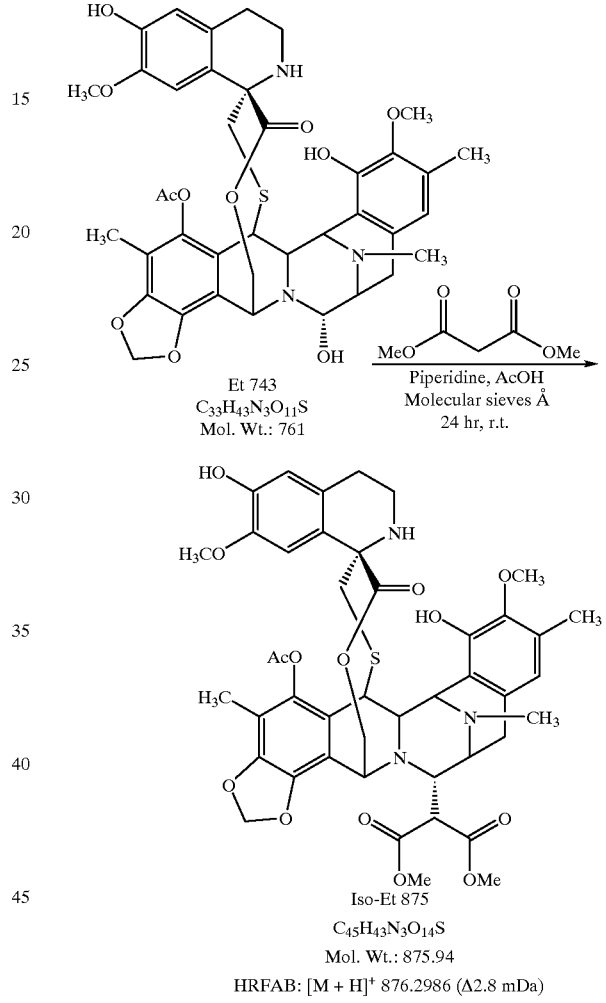

Figures 10A, 10B:
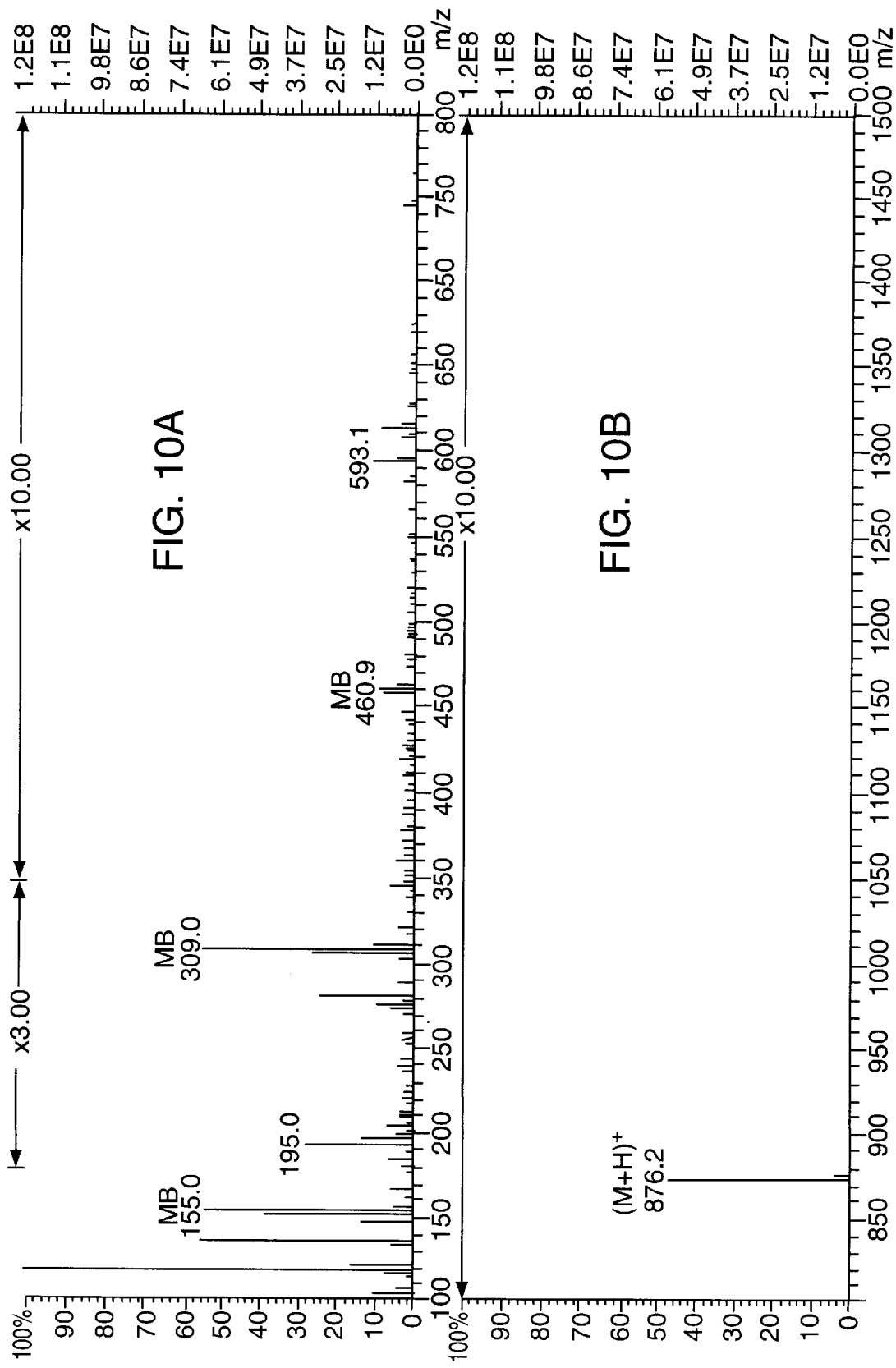
FIGS. 10A and 10B show the LRFAB Mass Spectrum of Et 875 in MB.
Figure 11:
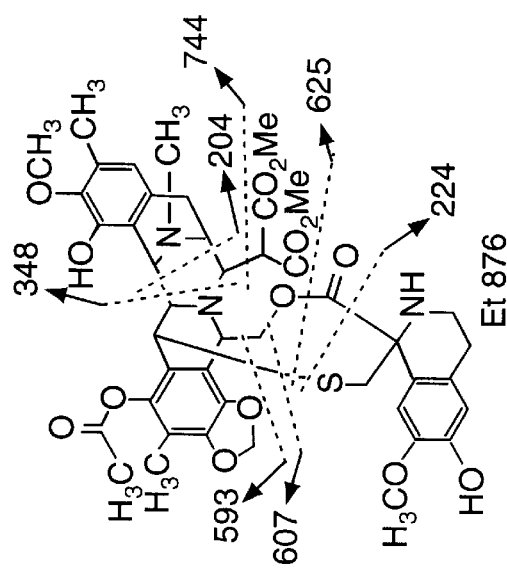
FIG. 11 shows the tandem FABMS/MS spectrum of Et 875 in MB.
Figure 11:
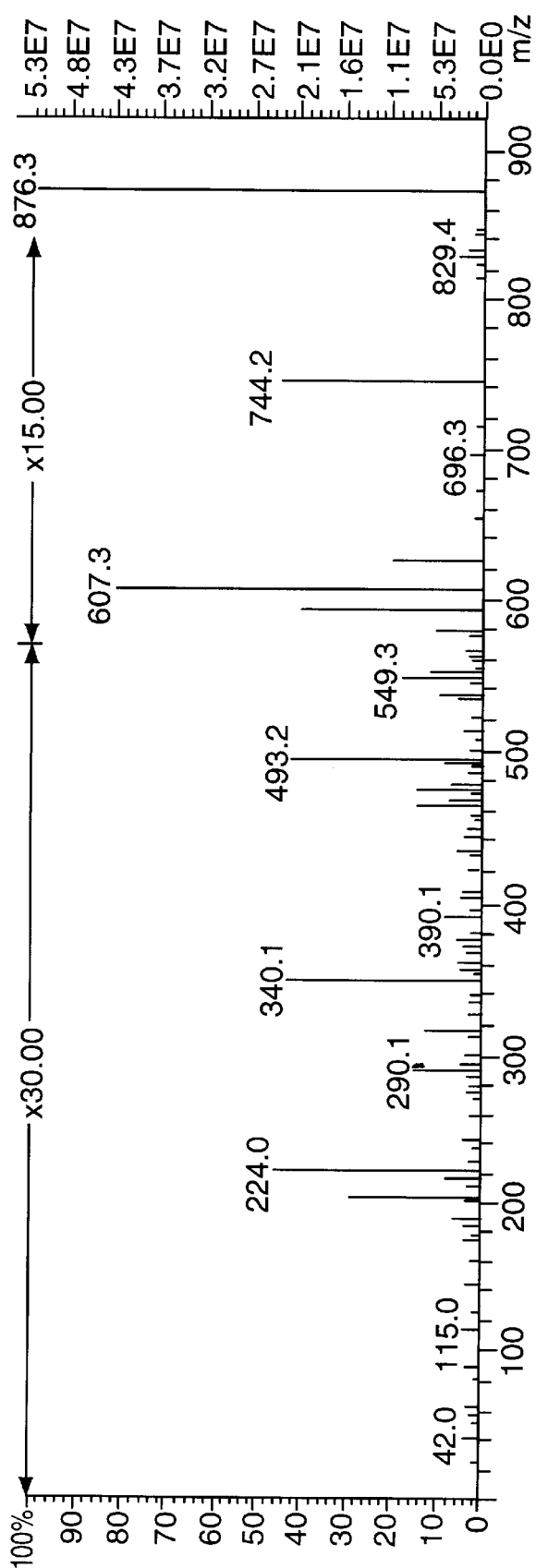

Glacial acetic acid (5 μL of a 28% $AcOH/CH_3CN$ solution, 4 eq) was added to a mixture of Et 743 (0.9 mg, 0.001 mmol, 1 eq), piperidine (5 μL of a 2% piperidine/$CH_3CN$ solution, 0.001 mmol, 1 eq), dimethyl malonate (5 μL of a 3% dimethyl malonate/$CH_3CN$ solution, 0.001 mmol, 1 eq) and crushed activated 4 Å molecular sieves (~0.5 mg) in $CH_3CN$ and the resulting suspension was stirred at room temperature for 24 hours. The reaction was filtered and the filtrate was concentrated to dryness. The residue was purified by flash chromatography (gradient elution: 100% $CHCl_3$→90% $CHCl_3$/MeOH) to yield Et 875 (180 μg, 20%, $R_f$ 0.53 in 90% $CHCl_3$/MeOH); HRFABMS, Calcd for $C_{44}H_{50}N_3O_{14}S$ $[M+H]^+$ m/z 876.3013, Found 876.2986, see FIGS. 10 and 11.

EXAMPLE 4
Semi-synthesis of Et 1560 (Et 729 dimer)

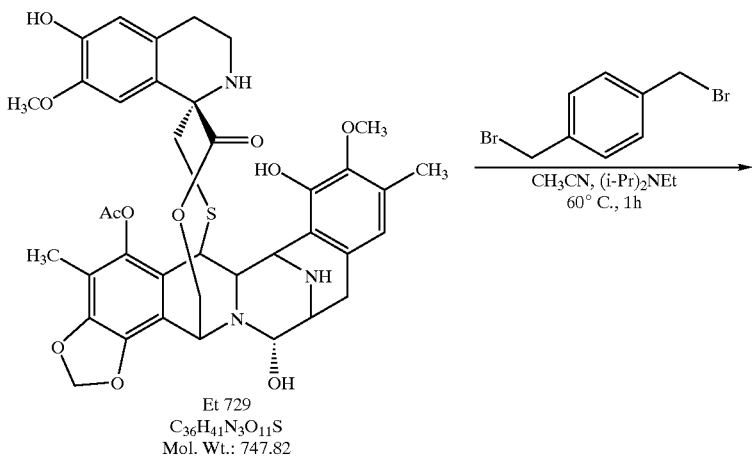

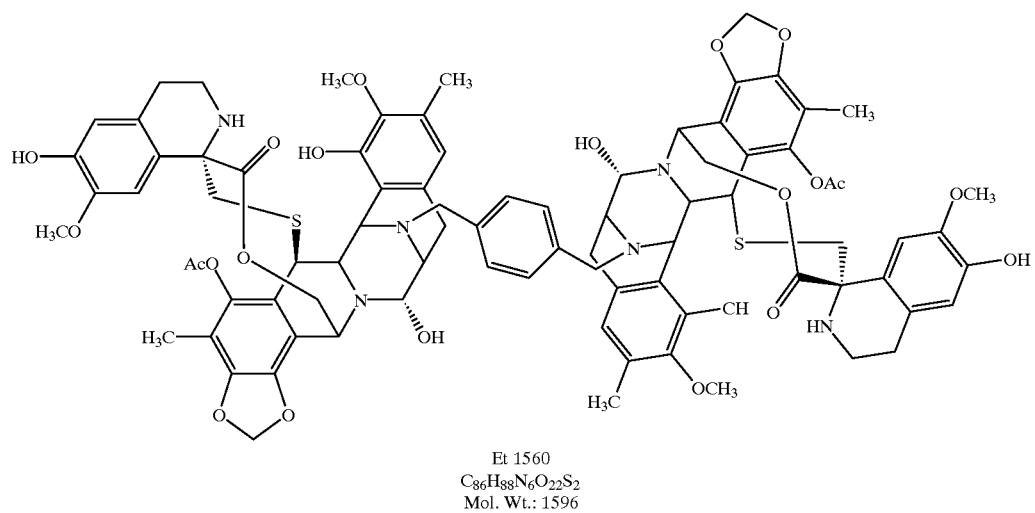

Figure 12:
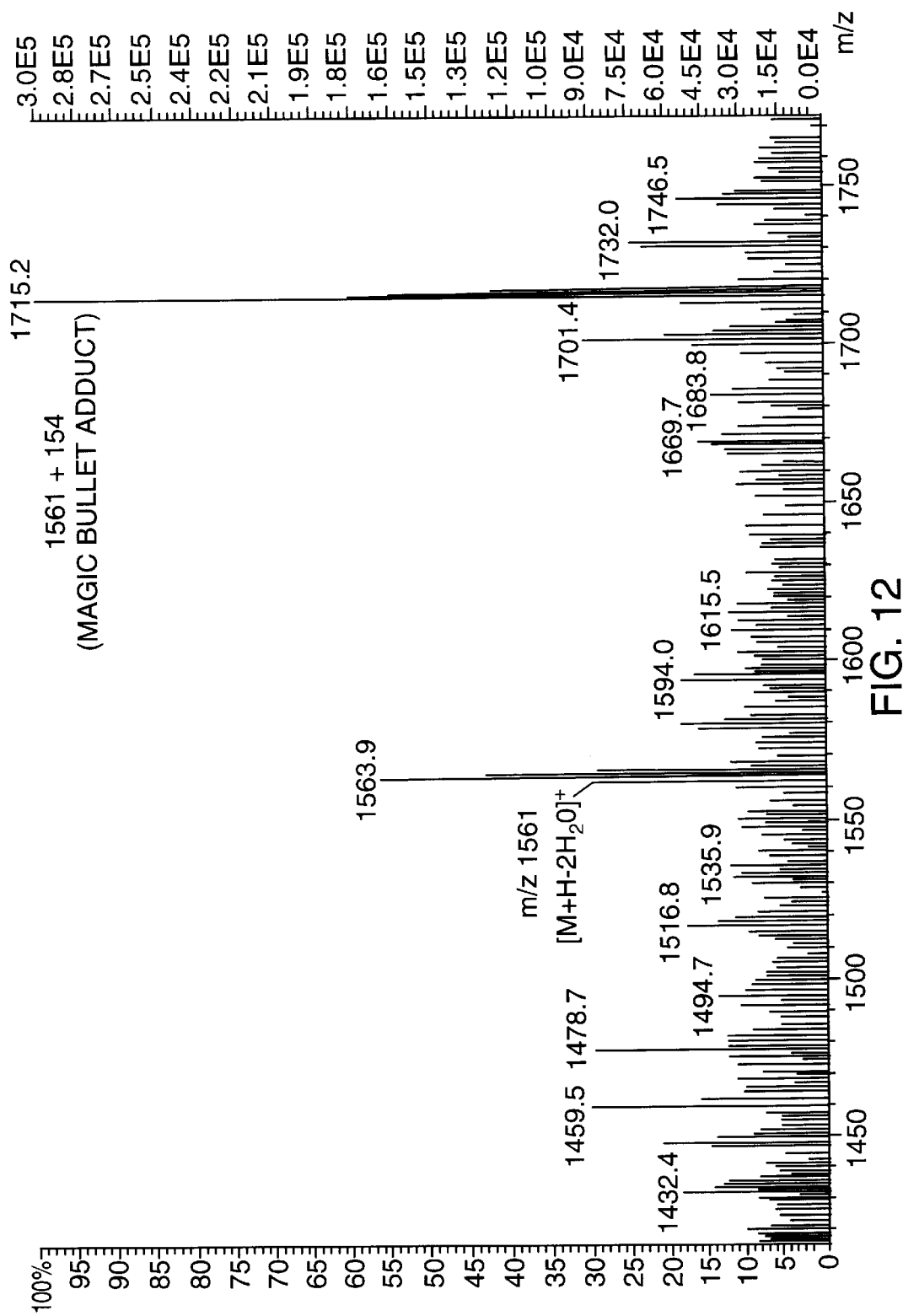
FIG. 12 shows the LRFAB Mass Spectrum of Et 1560 in MB.

To a reaction flask containing Et 729 (2.4 mg, 0.0032 mmol, 2 eq), diisopropylamine (2 μL) and CH$_3$CN (75 μL) and a magnetic stirrer was added α,α'-dibromo-p-xylene (34 μL of a 12.5 μg/μL α,α'-dibromo-p-xylene/CH$_3$CN solution, 0.0016 mmol, 1 eq) and the resulting solution was stirred at 60° C. for 1 hour. The reaction mixture was concentrated to dryness under a nitrogen stream. The residue purified by flash chromatography (gradient elution: 100% CHCl$_3$→90% CHCl$_3$/MeOH) to yield Et 1560 (300 μg, 12%, R$_f$ 0.53 in 90% CHCl$_3$/MeOH); HRFABMS, Calcd for C$_{84}$H$_{85}$N$_6$O$_{20}$S$_2$ [M+H−2H$_2$O]$^+$ m/z 1561.5260, Found 1561.5221, see FIG. 12.

BIOLOGICAL ACTIVITIES

As described above, the ecteinascidins are highly functionalized bis- or tris-(tetrahydroisoquinoline) alkaloids that exhibit potent in vivo antitumor activity. These compounds have chiefly been isolated as natural products from the mangrove tunicate *Ecteinascidia turbinata*, which grows throughout the Caribbean and the Gulf of Mexico. The major product of most extractions, Et 743, is currently undergoing Phase I clinical trials for treatment of human solid tumors. See for example, Kuffel et al., *Proceedings of the American Association for Cancer Research*, 38: 596 (1997); Moore et al., *Proceedings of the American Association for Cancer Research*, 38: 314 (1997); Mirsalis et al., *Proceedings of the American Association for Cancer Research*, 38: 309 (1997); Reid et al., *Cancer Chemotherapy and Pharmacology*, 38: 329–334 (1996); Faircloth et al., *European Journal of Cancer*, 32A, Supp. 1, pp. S5 (1996); Garcia-Rocha et al., *British Journal of Cancer*, 73: 875–883 (1996); Eckhardt et al., *Proceedings of the American Association for Cancer Research*, 37: 409 (1996); and Hendriks et al., *Proceedings of the American Association for Cancer Research*, 37: 389 (1996).

In view of the exceptional antitumor properties of the natural ecteinascidins, the present invention has studied the antitumor activities of the semi-synthetic analogs prepared herein. Table I shows the in vitro cytotoxic activities of the new Et compounds compared to the activity of two natural products, Et 743 and Et 729:

TABLE I

| Compound Name | Cytotoxicity to L1210 murine leukemia | |
|---|---|---|
| | IC$_{50}$ | IC$_{50}$(Et 743)/IC$_{50}$ |
| Et 729 | 0.05 | 10 |
| Et 743 | 0.5 | 1 |
| Et 757 | 0.01 | 50 |

TABLE I-continued

| | Cytotoxicity to L1210 murine leukemia | |
|---|---|---|
| Compound Name | $IC_{50}$ | $IC_{50}$(Et 743)/$IC_{50}$ |
| Iso-Et 743 | 0.03 | 17 |
| Boc-Et 729 | 5.0 | 0.1 |
| Et 1560 | 2.0 | 0.25 |
| Et 875 | 0.5 | 1 |

As shown by the in vitro data presented in Table I, the new compounds of the present invention possess cytotoxic activities levels up to 10 times better than those of two natural ecteinascidin compounds. Accordingly, it is expected that these compounds will also prove useful as pharmaceutical compositions for the treatment of mammalian, and particularly, human tumors in vivo.

REFERENCES

The following publications are cited as additional background information. To the extent necessary to allow a complete understanding of this invention, each is hereby incorporated herein by reference:

1. Rinehart, K. L. et al., *J. Nat. Prod.*, 53: 771–791 (1990).
2. Wright, A. E. et al., *J. Org. Chem.*, 55: 4508–4512 (1990).
3. Sakai et al., *Proc. Nat. Acad. Sci. U.S.A.*, 89: 11456–11460 (1992).
4. Rinehart et al., *J. Org. Chem.*, 55: 4512–4515 (1990).

The present invention has been described in detail, including the preferred embodiments thereof. However, it will be appreciated that those skilled in the art, upon consideration of the present disclosure, may make modifications and/or improvements on this invention and still be within the scope and spirit of this invention.

What is claimed is:

1. The compound Et 757, which has the following structure:

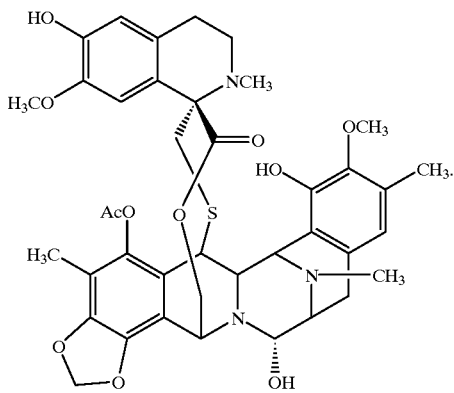

2. The compound Boc-Et 729, which has the following structure:

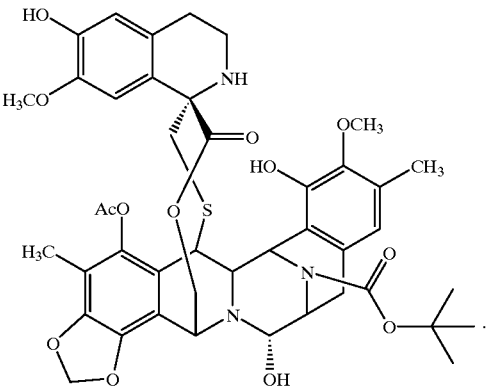

3. The compound Iso-Et 743, which has the following structure:

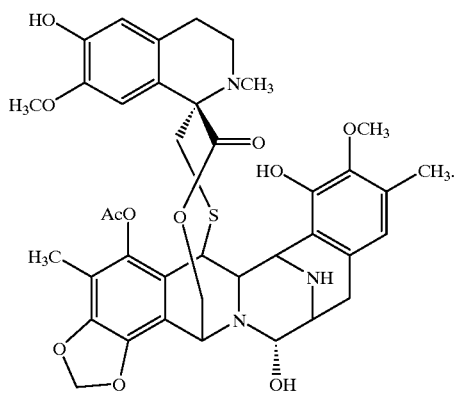

4. The compound Et 875, which has the following structure:

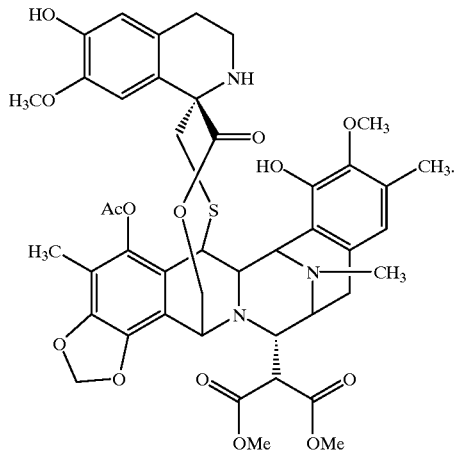

5. The compound Et 1560, which has the following structure:

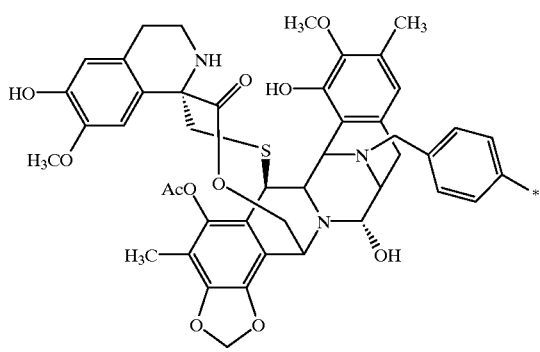

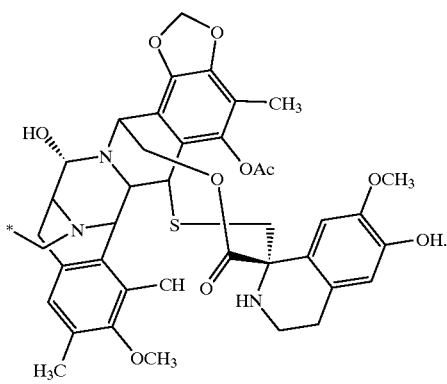

6. A pharmaceutical composition comprising the compound Et 757 and a pharmaceutically acceptable diluent, carrier, or excipient.

7. A pharmaceutical composition comprising the compound Boc-Et 729 and a pharmaceutically acceptable diluent, carrier, or excipient.

8. A pharmaceutical composition comprising the compound Iso-Et 743 and a pharmaceutically acceptable diluent, carrier, or excipient.

9. A pharmaceutical composition comprising the compound Et 875 and a pharmaceutically acceptable diluent, carrier, or excipient.

10. A pharmaceutical composition comprising the compound Et 1560 and a pharmaceutically acceptable diluent, carrier, or excipient.

11. A method of treating a patient suffering from a mammalian tumor selected from the group consisting of mammalian leukemia, mammalian melanoma and mammalian lung carcinoma, comprising administering to said patient, an effective antitumor amount of carcinoma, comprising administering to said patient, an effective antitumor amount of the substantially pure compound designated herein as Et 757 and a pharmaceutically acceptable carrier, diluent or excipient.

12. A method of treating a patient suffering from a mammalian tumor selected from the group consisting of mammalian leukemia, mammalian melanoma and mammalian lung carcinoma, comprising administering to said patient, an effective antitumor amount of the substantially pure compound designated herein as Boc-Et 729 and a pharmaceutically acceptable carrier, diluent or excipient.

13. A method of treating a patient suffering from a mammalian tumor selected from the group consisting of mammalian leukemia, mammalian melanoma and mammalian lung carcinoma, comprising administering to said patient, an effective antitumor amount of the substantially pure compound designated herein as Iso-Et 743 and a pharmaceutically acceptable carrier, diluent or excipient.

14. A method of treating a patient suffering from a mammalian tumor selected from the group consisting of mammalian leukemia, mammalian melanoma and mammalian lung carcinoma, comprising administering to said patient, an effective antitumor amount of the substantially pure compound designated herein as Et 875 and a pharmaceutically acceptable carrier, diluent or excipient.

15. A method of treating a patient suffering from a mammalian tumor selected from the group consisting of mammalian leukemia, mammalian melanoma and mammalian lung carcinoma, comprising administering to said patient, an effective antitumor amount of the substantially pure compound designated herein as Et 1560 and a pharmaceutically acceptable carrier, diluent or excipient.

* * * * *